US009506839B2

(12) United States Patent
Clayton et al.

(10) Patent No.: US 9,506,839 B2
(45) Date of Patent: Nov. 29, 2016

(54) RETAINING RING ONLINE INSPECTION APPARATUS AND METHOD

(71) Applicant: Siemens Energy, Inc., Orlando, FL (US)

(72) Inventors: Peter Jon Clayton, Casselberry, FL (US); Albert C. Sismour, Jr., Casselberry, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 206 days.

(21) Appl. No.: 14/275,122

(22) Filed: May 12, 2014

(65) Prior Publication Data

US 2015/0323469 A1    Nov. 12, 2015

(51) Int. Cl.
  *G01M 13/00* (2006.01)
  *G01N 21/88* (2006.01)
  *G02B 23/26* (2006.01)
  *G01N 21/954* (2006.01)

(52) U.S. Cl.
  CPC .......... *G01M 13/00* (2013.01); *G01N 21/8806* (2013.01); *G01N 21/8851* (2013.01); *G01N 21/954* (2013.01); *G02B 23/26* (2013.01); *G01N 2201/0692* (2013.01); *G01N 2201/08* (2013.01)

(58) Field of Classification Search
  CPC .......................... G01N 21/8851; G01M 13/00
  See application file for complete search history.

(56) References Cited

U.S. PATENT DOCUMENTS

| | | | |
|---|---|---|---|
| 4,572,663 A | 2/1986 | Greene et al. | |
| 5,517,861 A | 5/1996 | Haas et al. | |
| 6,992,315 B2 | 1/2006 | Twerdochlib | |
| 7,489,811 B2 | 2/2009 | Brummel et al. | |
| 7,619,728 B2 | 11/2009 | Ogburn et al. | |
| 8,076,909 B2 | 12/2011 | Diatzikis et al. | |
| 2004/0128109 A1* | 7/2004 | Saito | F01D 21/003 702/185 |
| 2006/0038988 A1* | 2/2006 | Thermos | G01N 21/954 356/241.1 |
| 2008/0158348 A1 | 7/2008 | Karpen et al. | |
| 2011/0184661 A1* | 7/2011 | Reed | G01B 11/14 702/34 |

* cited by examiner

*Primary Examiner* — Tung Vo
*Assistant Examiner* — Rowina Cattungal

(57) ABSTRACT

Inspecting a retaining ring of a dynamoelectric machine includes placing an optical device in a stationary component of the dynamoelectric machine and directing the optical device toward a radial view of the retaining ring. An image is obtained and transmitted of a circumferential portion of the retaining ring, using the optical device during rotation of the rotor. Identification is made of a location of one or more stress cracks forming and visible at the circumferential portion of the annular edge. Further, a structural condition is determined for at least one location on the retaining ring using a metric to identify a value of the metric exceeding a predetermined acceptable value of the metric.

16 Claims, 4 Drawing Sheets

US 9,506,839 B2

RETAINING RING ONLINE INSPECTION APPARATUS AND METHOD

FIELD OF THE INVENTION

The present invention relates to the field of dynamoelectric machines and, more particularly, to online inspection of dynamoelectric machines.

BACKGROUND OF THE INVENTION

Dynamoelectric machines such as turbine generators typically employ a retaining ring to contain a generator's rotor end windings. Such a ring, for example, may be constructed of a steel alloy and is generally attached to a generator's rotor body by an interference fit. The rotor end windings and the rotation forces developed during synchronous operating speeds tend to apply large amounts of stress to portions of the retaining ring. Because such stress forces are expected, retaining rings tend to be designed in such a way that any cracks which can eventually lead to ring failure are typically visible before ring failure occurs. In other words, there is a critical crack size such that cracks larger than that size are indicative of an impending failure of the retaining ring and that cracks can be smaller than this critical crack size, yet still be visibly detectable.

One method of inspecting a retaining ring for visible cracks involves shutting down the generator to a complete stop. The stopped unit may take upwards of 24 hours before it is cool enough to comfortably disassemble. Once disassembled, the unit can be inspected such as by using bore scopes to inspect difficult to reach portions of the generator. Once inspection is complete, then the unit can be reassembled which takes additional time before the generator can be restarted. In a worst case scenario, if a crack in the retaining ring exceeds the critical crack size before an outage and inspection of the generator can be completed, the retaining ring may fail causing severe damage to the rotating and stationary components of the generator.

SUMMARY OF THE INVENTION

One aspect of the present invention relates to a system for inspecting a retaining ring of a dynamoelectric machine that includes an optical device in a stationary component of the dynamoelectric machine directed toward a radial view of the retaining ring; wherein the retaining ring includes a cylindrical body positioned on a rotatable rotor of the dynamoelectric machine, the cylindrical body including an annular edge having a radial height. The optical device also includes a first optical fiber bundle for providing illumination to the radial view of the retaining ring and a second optical fiber bundle for capturing reflected illumination thereby obtaining and transmitting an image of a circumferential portion of the annular edge of the retaining ring. An image analyzer is included which identifies a location of one or more stress cracks forming and visible at the circumferential portion of the annular edge; the image analyzer further determines a structural condition for at least one location on the retaining ring using a metric including one or more of a) a measured stress crack length, b) a measured stress crack width, and c) a counted number of stress cracks on the annular edge. The system further includes a comparator for identifying when the structural condition for the at least one location exceeds a predetermined acceptable value for the metric.

Another aspect of the present invention relates to a method for inspecting a retaining ring of a dynamoelectric machine that includes placing an optical device in a stationary component of the dynamoelectric machine and directing the optical device toward a radial view of the retaining ring; wherein the retaining ring includes a cylindrical body positioned on a rotatable rotor of the dynamoelectric machine, the cylindrical body including an annular edge having a radial height. The method also includes obtaining and transmitting an image of a circumferential portion of the annular edge of the retaining ring, using the optical device during rotation of the rotor; and identifying a location of one or more stress cracks forming and visible at the circumferential portion of the annular edge. Further the method includes determining a structural condition for at least one location on the retaining ring using a metric including one or more of a) a measured stress crack length, b) a measured stress crack width, and c) a counted number of stress cracks on the annular edge; and using the structural condition for the at least one location to identify a value of the metric for the retaining ring exceeding a predetermined acceptable value for the metric.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Embodiments of the present invention can be used in all sections of a gas turbine engine (fan, compressor, and turbine) and on other turbo-machinery equipment including, but not limited to, power turbines or aero turbines. Furthermore, various rotating regions within a dynamoelectric machine can be imaged and analyzed in accordance with the principles of the present invention. However, the description below mainly focuses on describing one example location within a machine that includes an end retaining ring. However, one of ordinary skill will recognize that other regions of the machine can be imaged as well without departing from the scope of the present invention.

Figure 1:
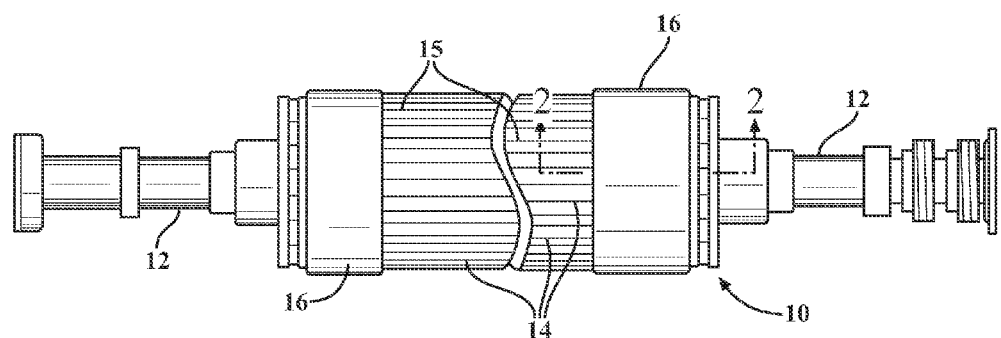
FIG. 1 is a diagrammatic view illustrating a rotor having end retaining rings in accordance with the principles of the present invention.
Figure 2:
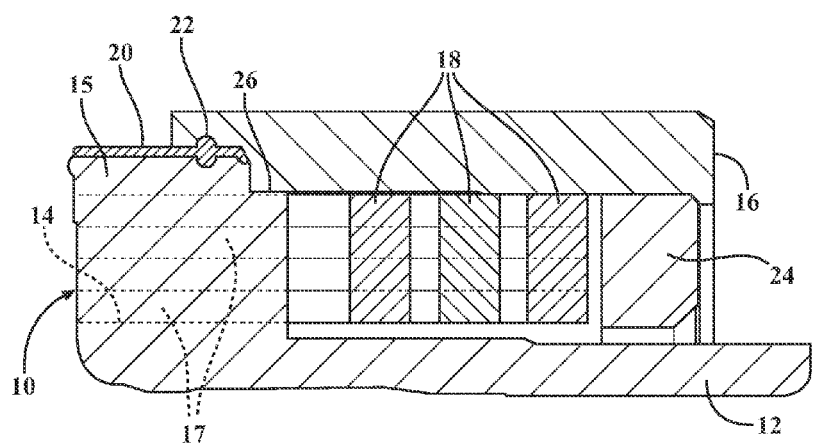
FIG. 2 is a more detailed view of the end retaining ring, taken along line 2-2 in FIG. 1.

A rotor 10 illustrative of the type used in turbine-driven generators is depicted in FIGS. 1 and 2. The rotor 10 is generally a large cylindrical body from which spindles 12 extend for rotatably supporting the rotor 10. The rotor 10 has a series of longitudinal (axially-extending) slots 14 machined radially into its outer circumference, which results in radially-extending teeth 15 being defined along the perimeter of the rotor 10. Field windings 17, comprising multiple insulated conductor bars, can be installed in the slots 14 to extend the length of the rotor 10, longitudinally projecting from each end 26 of the rotor 10. The field windings 17 include end turns 18 (FIG. 2), each of which electrically connects the longitudinal portion of a winding in one slot 14 with the longitudinal portion of a winding in a further slot 14. The field windings 17 do not fill the entire slot 14, which typically has a tapered region so that the slot 14 is narrower at the perimeter of the rotor 10. Wedges (not shown) are placed in the tapered region of each slot 14 to hold the windings 17 in place against centrifugal forces exerted when the rotor 10 rotates.

As the rotor 10 spins, the end turns 18 are also subjected to centrifugal forces that force the end turns 18 radially outward. This radial movement of the end turns 18 is confined by retaining rings 16 that are attached to the ends of the rotor 10 to enclose the end turns 18, as shown in FIG. 2. As is widely practiced, retaining rings 16 of the type shown in FIG. 2 are attached to the ends of the rotor 10 by shrink fitting. In FIG. 2, the inboard end of the retaining ring 16 is shrink-fit around a shoulder 20 defined on the rotor 10, and a locking key 22 can be provided between the ring 16 and rotor 10 to prevent axial movement of the ring 16. The retaining ring 16 can also be supported at its outboard end with a centering ring 24, onto which the ring 16 is also preferably shrink-fitted.

Centrifugal forces generated as a result of the spinning rotor 10 cause the end turns 18 to press firmly against the inside surface of each retaining ring 16, applying a considerable force to the rings 16. Consequently, the retaining rings 16 are typically formed of a high-strength, nonmagnetic steel such as 1818 steel material. As rotor diameters and spin speeds increase, so do the centrifugal forces applied to the rings 16 by the end turns 18.

Figure 3:
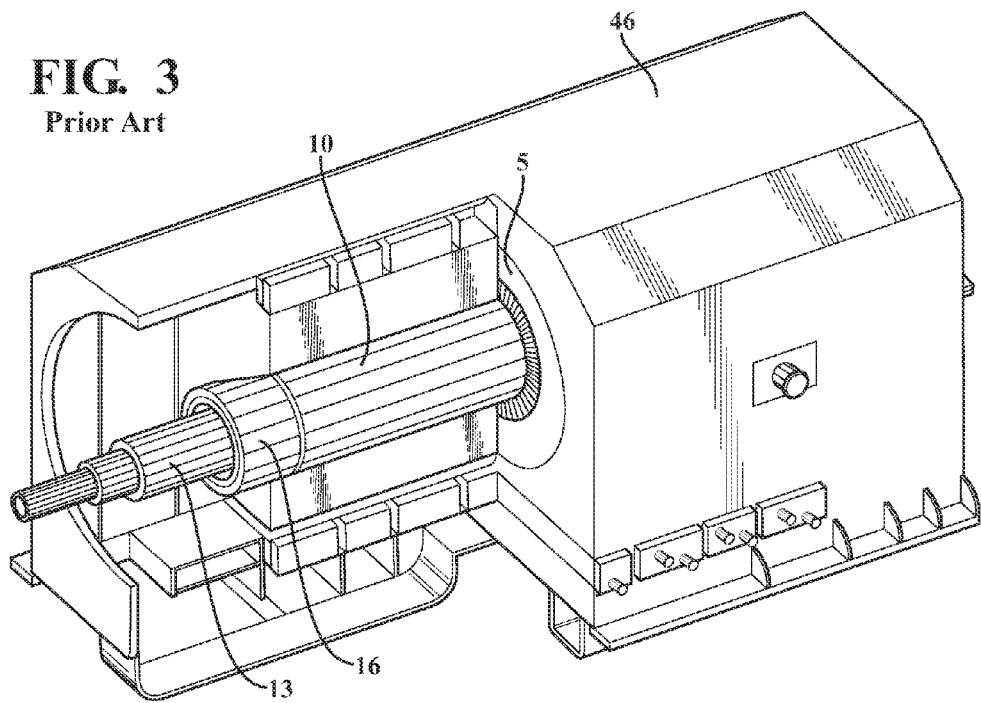
FIG. 3 illustrates how the rotor of FIG. 1 can be arranged with respect to a stator of a dynamoelectric machine in accordance with the principles of the present invention.

As shown, in FIG. 3, a turbine generator, or other dynamoelectric machine, is generally constituted by the rotor 10 supported by a rotation shaft 13, and a stator 5 located around the rotor 10. As mentioned, a retaining ring 16 can be fixedly fitted into an end portion of the rotor winding in the axial direction so as to cover the end portion, and this retaining ring 16 retains a centrifugal force of the conductors. Additionally, in general, a temperature of the portion near the retaining ring 16 is relatively high such that cooling with air or hydrogen is often employed.

Figure 4:
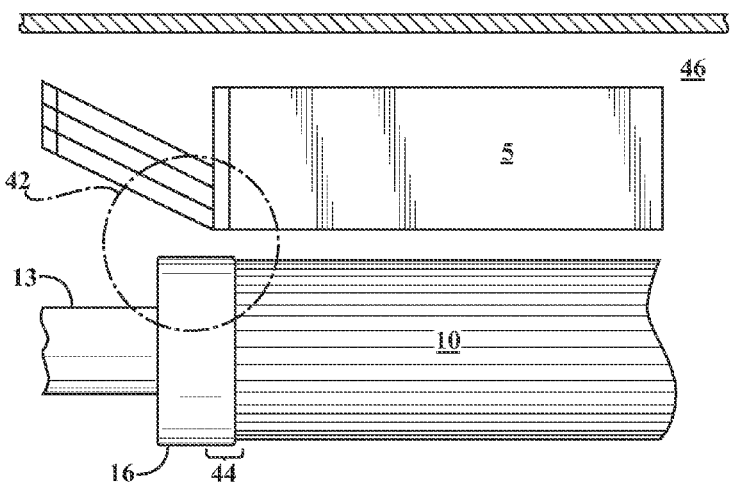
FIG. 4 is a schematic view of an area of an end retaining ring to be imaged in accordance with the principles of the present invention.

FIG. 4 is a schematic view of an area of an end retaining ring to be imaged in accordance with the principles of the present invention. Within a machine housing 46 the rotor 10 is shown in relation to a portion of the stator 5. As already mentioned the rotor 10 is coupled to the shaft 13 and includes the end retaining ring 16. A region generally denoted by the circle 42 includes a surface on a circumference of the end retaining ring that is substantially parallel to a major-axis of the shaft 13 and the rotor 10. Retaining ring stress cracks that can be viewed in this region 42 of the machine of FIG. 4 are particularly beneficial in evaluating structural condition of the end retaining ring 16. More particularly, stress cracks appearing in, or near, a nose portion 44 are beneficial to identify and analyze for such purposes.

Figure 5:
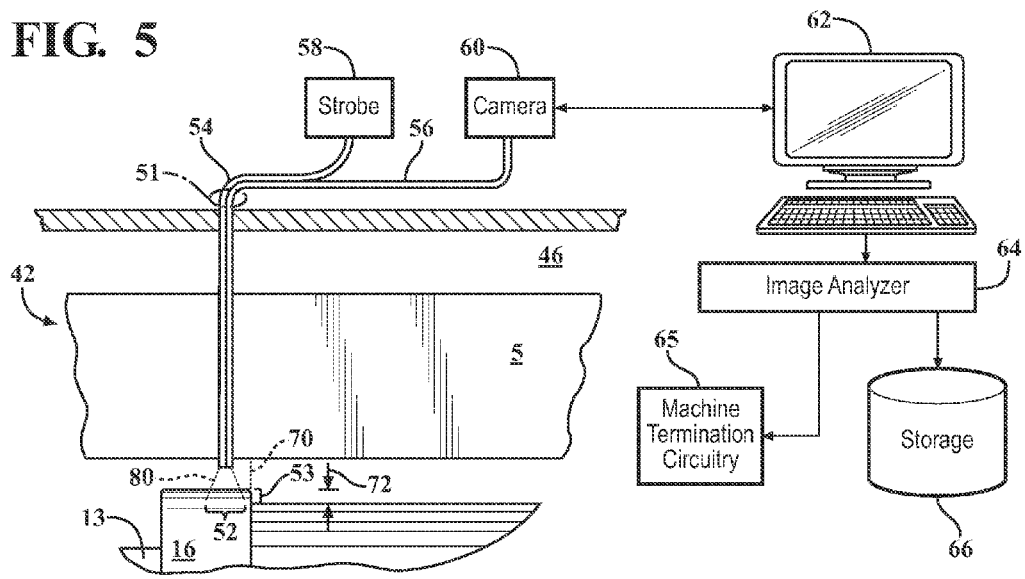
FIG. 5 provides a block-level diagram of components to image an end retaining ring image portion in accordance with the principles of the present invention.

FIG. 5 provides a block-level diagram of components to image an end retaining ring image portion in accordance with the principles of the present invention. The system for inspecting a retaining ring of a dynamoelectric machine, as shown in FIG. 5, includes an optical device 51 in a stationary component (e.g., stator 5) of the dynamoelectric machine directed toward a radial view 80 of the retaining ring 16; wherein the retaining ring 16 includes a cylindrical body positioned on a rotatable rotor 10 of the dynamoelectric machine, the cylindrical body including an annular edge 70 having a radial height 72. This radial view 80 of the retaining ring 16 includes a view of a circumferential portion 52 of the annular edge 70. One of ordinary skill will recognize that the optical device 51 could be positioned differently within the stator 5 so that the radial view 80 includes different portions of the rotor, retaining ring, and other machine components. For example, the radial view 80 could include an end portion 53 near the annular edge 70.

It should be understood that, as used herein, "radial view" refers to a viewing direction that is directed radially inward from a position located on a radial line, i.e., perpendicular to the major-axis of the shaft 13 and the rotor 10, spaced outward from the rotor 10.

The optical device 51 can include a first optical fiber bundle 54 for providing illumination to the radial view of the retaining ring 16 and a second optical fiber bundle 56 for capturing reflected illumination thereby obtaining and transmitting an image of a circumferential portion 52 of the annular edge of the retaining ring. The optical fiber bundle 54 can be a single fiber or multiple fibers that transmit light from a light source 58 (e.g., a strobe light) towards the radial view 80. In this way, the circumferential portion 52 can be illuminated. The other fiber bundle 56 can include a plurality of optical fibers such that the ends of the fibers closest to the retaining ring 16 capture illumination that is reflected from the circumferential portion 52. This reflected illumination can then be transmitted to a camera 60 by the plurality of optical fibers. In this way, the camera 60 (e.g., video or still image) can capture images of the circumferential portion 52 transmitted by the optical fiber bundle 56. As known to one of ordinary skill, one or both of the ends of the second optical fiber bundle 56 can include lenses and other optical components that help generate a well-focused image that can be captured by the camera 60.

The camera 60 can be in communication with a computer 62 and/or an image analyzer 64. Based on the image(s) captured by the camera 60, the image analyzer 64 can identify a location of one or more stress cracks forming and visible at the circumferential portion 52 of the annular edge 70. The computer 62 can include a display that allows an operator to view the images from the camera 60. The image analyzer 64 can be part of the computer 62 but could also be a separate apparatus without departing from the scope of the present invention.

Figure 7:
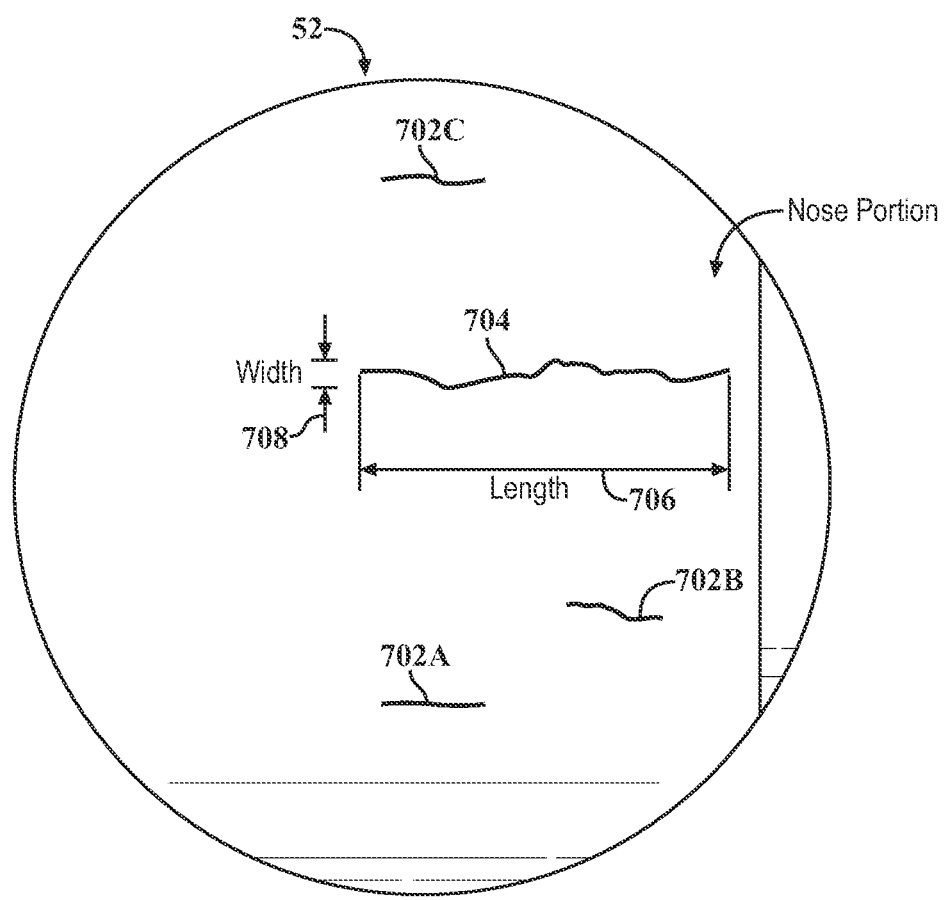
FIG. 7 illustrates example cracks on a nose portion of an end retaining ring that can be imaged in accordance with the principles of the present invention.

In addition to identifying any stress cracks, the image analyzer 64 can determine a structural condition for at least one location on the retaining ring 16 using a metric including one or more of a) a measured stress crack length, b) a measured stress crack width, and c) a counted number of stress cracks near the annular edge 70. Referring to FIG. 7, an example image of the circumferential portion 52 shows stress cracks 702A, 702B, 702C. In particular, a crack 704 is shown that is generally in a direction parallel with the major-axis of the rotor 10. The crack 704 has a length 706 and a width 708. The image analyzer 64 is configured to analyze a captured image to distinguish stress crack portions (e.g., 702A-702C) from normal surface portions of the retaining ring 16. Also, based on the known design attributes of the optical components that capture the image of the circumferential portion 52, the length 706 and width 704 of any stress cracks can be automatically determined from the captured image.

The stress cracks (as shown in FIG. 7) can be an indicator of the structural condition of the retaining ring 16. By analyzing the stress cracks, a determination can be made whether the retaining ring 16 is nearing a catastrophic failure or has a significant operational lifetime remaining. By capturing the images while the rotor is operational and rotating, analysis and inspection of the retaining ring 16 can be accomplished without the typical delays and inconveniences of traditional inspection techniques.

A variety of different metrics for structural conditions are contemplated within the scope of the present invention. One example metric is the length 706 of the crack 704. According to this metric, the length 704 is indicative of the structural condition of the retaining ring. As such, a retaining ring having at least one crack with a length greater than a predetermined amount can be considered as having an unsafe, or unacceptable, structural condition. The predetermined amount that indicates an unsafe structural condition will vary based on the design of each particular dynamoelectric machine. It may be understood that, for any machine, the crack being monitored will be one which is sufficiently sized to be visually detected. Other metrics can include the crack width 708 such that a crack exceeding a maximum allowable width would cause the retaining ring to be deemed unsafe, or in a deteriorated condition. Additionally, a metric can include a combination of crack attributes. For example, even if the crack length was less than an allowable length but the crack width was over a certain value, then the metric could indicate an unacceptably deteriorated retaining ring. The metric might even include the number of cracks as some factor in determining the structural condition of the retaining ring such that small cracks in a relatively large number might also be considered evidence of an unacceptable structural condition of the retaining ring. Hence, it may be understood that a predetermined threshold value for the metric may be used to determine an unacceptable structural condition for the retaining ring, where the predetermined threshold value can include one or more observed crack characteristics, or a combination of crack characteristics associated with an unacceptable structural condition, e.g., indicating that a potential for failure of the retaining ring is at an unacceptable level.

The image analyzer 64, or the computer 62, can include a comparator, or similar circuitry, for identifying when the structural condition for the at least one location exceeds a predetermined acceptable structural condition as defined by the predetermined threshold value. In some instances, then, the image analyzer 64 can communicate with circuitry 65 that automatically terminates operation of the dynamoelectric machine.

As shown in FIG. 5, a storage device 66 may be connected with the computer 62 and the image analyzer 64. The storage device 66 can be utilized to store images that are captured by the camera 60. Using the stored images, the image analyzer can compare images captured at different times. This comparison of the history, or chronological progression, of how a retaining ring is changing can be useful in determining how fast a crack is growing. The rate that a crack grows can also be included in the metric noted above when determining the structural condition of the retaining ring.

Figure 6:
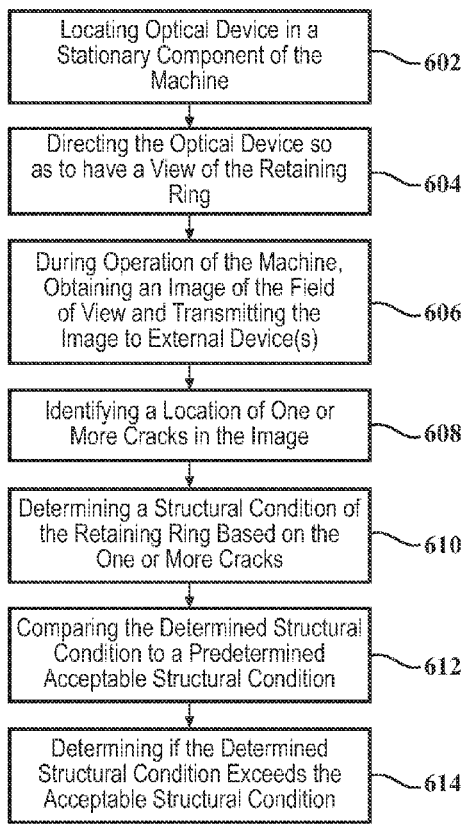
FIG. 6 is a flowchart of an example method of analyzing an end retaining ring in accordance with the principles of the present invention.

FIG. 6 is a flowchart of an example method of analyzing an end retaining ring in accordance with the principles of the present invention. The method for inspecting a retaining ring of a dynamoelectric machine includes placing an optical device, in step 602, in a stationary component of the dynamoelectric machine and directing, in step 604, the optical device toward a radial view of the retaining ring. As described above, the retaining ring includes a cylindrical body positioned on a rotatable rotor of the dynamoelectric machine, the cylindrical body including an annular edge having a radial height. Next, in step 606, the optical device is used during rotation of the rotor to obtain and transmit an image of a circumferential portion of the annular edge of the retaining ring. From the transmitted image, an identification is made, in step 608, of a location of one or more stress cracks forming and visible at the circumferential portion of the annular edge. A structural condition is determined, in step 610, for at least one location on the retaining ring using a metric including one or more of a) a measured stress crack length, b) a measured stress crack width, and c) a counted number of stress cracks near the annular edge.

Next, in step 612, a comparison is made using the structural condition for the at least one location to identify, in step 614, a structural condition for the retaining ring that exceeds a predetermined acceptable structural condition (e.g., crack length, crack size or number of cracks).

During operation of the dynamoelectric machine the rotor 10 rotates at a substantially constant speed when operating synchronously. For example, the rotor 10 can rotate at 3600 RPMs. Thus, a period of rotation is relatively constant. The strobe 58 (See FIG. 5) can be operated to take advantage of the consistent period of rotation. For example, if the strobe 58 illuminates the radial view 80 at the same rate as the RPMs (e.g., 3600 strobes a minute, or some integer division thereof), then the radial view 80 would always be of the same circumferential section 52 of the surface of the retaining ring 16. If, however, the strobe 58 is operated slightly non-synchronously with respect to the rotational period of the rotor 10, then a different circumferential portion 52 around the surface of the retaining ring 16 can be captured in each image.

For example, if a circumferential dimension of the field of view of the radial view 80 is approximately 1% of the entire circumference of the retaining ring 16, then operating the strobe 58 about 1% slower (or faster) that the rotational period of the rotor 10, will allow images to be captured sequentially of the retaining ring's entire circumference (within the field of the radial view 80).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for inspecting a retaining ring of a dynamoelectric machine, the method comprising:
   placing an optical device in a stationary component of the dynamoelectric machine and directing the optical device toward a radial view of the retaining ring;
   wherein the retaining ring includes a cylindrical body positioned on a rotatable rotor of the dynamoelectric machine, the cylindrical body including an annular edge having a radial height;

using the optical device during rotation of the rotor, obtaining and transmitting an image of a circumferential portion of the annular edge of the retaining ring;

identifying a location of one or more stress cracks forming and visible at the circumferential portion of the annular edge;

determining a structural condition for at least one location on the retaining ring using a metric including one or more of a) a measured stress crack length, b) a measured stress crack width, and c) a counted number of stress cracks on the annular edge; and comparing the structural condition for the at least one location on the retaining ring using a value of the metric with a predetermined acceptable value of the metric to identify whether the value of the metric exceeding the predetermined acceptable value of the metric, wherein the predetermined acceptable value of the metric comprises one or more of a predetermined acceptable value of a stress crack length, a predetermined acceptable value of a stress crack width, and predetermined acceptable value of a number of stress cracks on the annular edge.

2. The method of claim 1 comprising:
causing termination of operation of the dynamoelectric machine when the structural condition exceeds the predetermined acceptable value for the metric.

3. The method of claim 1, wherein the optical device is used during synchronous operation of the dynamoelectric machine.

4. The method of claim 1, wherein determining the value for the metric includes determining a crack progression over a chronological sequence of multiple events of obtaining and transmitting an image of the annular edge.

5. The method of claim 1, wherein the optical device includes an optical cable having a measurement end located at the stationary component, and an analysis end located at a signal generation and reception device.

6. The method of claim 5, wherein the signal generation and reception device includes a strobe light synchronized to rotational speed of the dynamoelectric machine.

7. The method of claim 1, wherein the image includes a portion of the radial height of the annular edge.

8. The method of claim 7, comprising:
identifying a location of one or more stress cracks forming and visible at the radial height portion of the annular edge.

9. A system for inspecting a retaining ring of a dynamoelectric machine, comprising:
an optical device in a stationary component of the dynamoelectric machine directed toward a radial view of the retaining ring;
wherein the retaining ring includes a cylindrical body positioned on a rotatable rotor of the dynamoelectric machine, the cylindrical body including an annular edge having a radial height;

the optical device including a first optical fiber bundle for providing illumination to the radial view of the retaining ring and a second optical fiber bundle for capturing reflected illumination thereby obtaining and transmitting an image of a circumferential portion of the annular edge of the retaining ring;

an image analyzer which identifies, based on the image, a location of one or more stress cracks forming and visible at the circumferential portion of the annular edge;

the image analyzer further determines a structural condition for at least one location on the retaining ring using a metric including one or more of a) a measured stress crack length, b) a measured stress crack width, and c) a counted number of stress cracks on the annular edge; and a comparator which compares the structural condition for the at least one location on the retaining ring using a value of the metric with a predetermined acceptable value of the metric to identify whether the value of the metric exceeds the predetermined acceptable value for of the metric, wherein the predetermined acceptable value of the metric comprises one or more of a predetermined acceptable value of a stress crack length, a predetermined acceptable value of a stress crack width, and predetermined acceptable value of a number of stress cracks on the annular edge.

10. The system of claim 9, comprising:
a terminating circuit causing termination of operation of the dynamoelectric machine when the structural condition exceeds the predetermined acceptable value for the metric.

11. The system of claim 9, wherein the optical device is used during synchronous operation of the dynamoelectric machine.

12. The system of claim 11, comprising:
an illumination device that comprises a strobe light synchronized to rotational speed of the dynamoelectric machine.

13. The system of claim 9, wherein determination of the value for the metric includes determining a crack progression over a chronological sequence of multiple images of the annular edge.

14. The system of claim 9, wherein the each of the first and second optical fibers include respective first ends located at the stationary component and respective second ends located outside of the dynamoelectric machine.

15. The system of claim 9, wherein the image includes a portion of the radial height of the annular edge.

16. The system of claim 15, wherein the image analyzer identifies a location of one or more stress cracks forming and visible at the radial height portion of the annular edge.

* * * * *